US00PP34786P2

(12) United States Plant Patent
van Sambeek

(10) Patent No.: US PP34,786 P2
(45) Date of Patent: Nov. 29, 2022

(54) ***GAURA* PLANT NAMED 'DOGAURGRABL'**

(50) Latin Name: *Gaura lindheimeri*
Varietal Denomination: Dogaurgrabl

(71) Applicant: DUMMEN GROUP B.V., De Lier (NL)

(72) Inventor: Ellen van Sambeek, Oegstgeest (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 17/831,425

(22) Filed: Jun. 2, 2022

(51) Int. Cl.
*A01H 5/02* (2018.01)
*A01H 6/00* (2018.01)

(52) U.S. Cl.
USPC ..... Plt./432
CPC ..... *A01H 6/00* (2018.05)

(58) Field of Classification Search
USPC ..... Plt./432
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Gaura* plant named 'Dogaurgrabl', characterized by its compact and upright plant habit; moderately vigorous growth habit and moderate growth rate; freely branching habit; freely flowering habit; white-colored flowers with light pink-colored apices; and good garden performance.

1 Drawing Sheet

Botanical designation: *Gaura lindheimeri.*
Cultivar denomination: 'DOGAURGRABL'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Feb. 4, 2022, application number 2022/0383. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Gaura* plant, botanically known as *Gaura lindheimeri* and hereinafter referred to by the name 'Dogaurgrabl'.

The new *Gaura* is a product of a planned breeding program conducted by the Inventor in Aalsmeer, The Netherlands. The objective of the breeding program is to create new compact and early-flowering *Gaura* plants with attractive leaf and flower coloration.

The new *Gaura* plant originated from a cross-pollination in June, 2016 in Aalsmeer, The Netherlands of a proprietary selection of *Gaura lindheimeri* identified as code number GR14-000046-006, not patented, as the female, or seed, parent with a proprietary selection of *Gaura lindheimeri* identified as code number GR14-000012-001, not patented, as the male, or pollen, parent. The new *Gaura* plant was discovered and selected by the Inventor as a single flowering plant from within the progeny of the stated cross-pollination in a controlled environment in Aalsmeer, The Netherlands in June, 2017.

Asexual reproduction of the new *Gaura* plant by vegetative tip cuttings in a controlled environment in Aalsmeer, The Netherlands since July, 2017 has shown that the unique features of this new *Gaura* plant are stable and reproduced true to type in successive generations.

SUMMARY OF THE INVENTION

Plants of the new *Gaura* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dogaurgrabl'. These characteristics in combination distinguish 'Dogaurgrabl' as a new and distinct *Gaura* plant:

1. Compact and upright plant habit.
2. Moderately vigorous growth habit and moderate growth rate.
3. Freely branching habit.
4. Freely flowering habit.
5. White-colored flowers with light pink-colored apices.
6. Good garden performance.

Plants of the new *Gaura* can be compared to plants of the female parent selection. Plants of the new *Gaura* differ from plants of the female parent selection in flower color as plants of the new *Gaura* have white-colored flowers with light pink-colored apices whereas plants of the female parent selection have pure white-colored flowers.

Plants of the new *Gaura* can be compared to plants of the male parent selection. Plants of the new *Gaura* differ from plants of the male parent selection in flower color as plants of the new *Gaura* have white-colored flowers with light pink-colored apices whereas plants of the male parent selection have pure white-colored flowers.

Plants of the new *Gaura* can be compared to plants of *Gaura lindheimeri* 'Belezza White', not patented. In side-by-side comparisons, plants of the new *Gaura* differ from plants of 'Belezza White' in the following characteristics:

1. Plants of the new *Gaura* are more compact than and not as tall as plants of 'Belezza White'.
2. Plants of the new *Gaura* have white-colored flowers with light pink-colored apices whereas plants of 'Belezza White' have pure white-colored flowers.

Plants of the new *Gaura* can also be compared to plants of *Gaura lindheimeri* 'Gaudi Red', not patented. In side-by-side comparisons, plants of the new *Gaura* differ from plants of 'Gaudi Red' in the following characteristics:

1. Plants of the new *Gaura* have green-colored leaves whereas plants of 'Gaudi Red' have reddish-colored leaves.
2. Plants of the new *Gaura* have white-colored flowers with light pink-colored apices whereas plants of 'Gaudi Red' have dark reddish pink-colored flowers.

BRIEF DESCRIPTION OF THE PHOTOGRAPH

The accompanying colored photograph illustrates the overall appearance of the new *Gaura* plant showing the colors as true as it is reasonably possible to obtain in colored reproductions of this type. Colors in the photograph may differ slightly from the color values cited in the detailed botanical description which accurately describe the colors of the new *Gaura* plant.

The photograph is a side perspective view of a typical plant of 'Dogaurgrabl' grown in a container.

DETAILED BOTANICAL DESCRIPTION

The aforementioned photographs and following observations, measurements and values describe plants grown during the autumn in 17-cm containers in an outdoor nursery in Aalsmeer, The Netherlands and under cultural practices typical of commercial *Gaura* production. During the production of the plants, day temperatures averaged 21° C. and night temperatures averaged 15° C. Plants were pinched one time one week after planting and were 24 weeks old when the photograph and description were taken. In the following description, color references are made to The Royal Horticultural Society Colour Chart, Fifth Edition, except where general terms of ordinary dictionary significance are used.

Botanical classification: *Gaura lindheimeri* 'Dogaurgrabl'.

Parentage:

*Female, or seed, parent*.—Proprietary selection of *Gaura lindheimeri* identified as code number GR14-000046-006, not patented.

*Male or pollen parent*.—Proprietary selection of *Gaura lindheimeri* identified as code number GR14-000012-001, not patented. PROPAGATION:

*Type*.—By vegetative tip cuttings.

*Time to initiate roots, summer*.—About ten days at temperatures about 26° C.

*Time to initiate roots, winter*.—About two weeks at temperatures about 23° C.

*Time to produce a rooted young plant, summer*.—About twelve days at temperatures about 23° C.

*Time to produce a rooted young plant, winter*.—About 16 days at temperatures about 18° C.

*Root description*.—Medium in thickness, fibrous; typically white to light yellow in color, actual color of the roots is dependent on substrate composition, water quality, fertilizer type and formulation, substrate temperature and physiological age of roots.

*Rooting habit*.—Moderately freely branching; dense.

Plant description:

*Plant and growth habit*.—Herbaceous perennial; compact and upright plant habit; freely basal branching habit with about six primary branches each with about ten secondary branches developing per plant, pinching enhances lateral branch development; dense and bushy plant form; moderately vigorous growth habit and moderate growth rate.

*Plant height*.—About 38 cm.

*Plant diameter*.—About 26 cm.

Lateral branch description:

*Length*.—About 30 cm.

*Diameter*.—About 2 mm.

*Internode length*.—About 1 cm.

*Strength*.—Strong.

*Aspect*.—Upright to about 60° from vertical.

*Texture and luster*.—Pubescent; semi-glossy.

*Color, developing*.—Close to 143A.

*Color, developed*.—Close to NN137A; if woody, close to 199A.

Leaf description:

*Arrangement*.—Alternate, simple; sessile.

*Length*.—About 5 cm.

*Width*.—About 1.2 cm.

*Shape*.—Linear.

*Apex*.—Acute.

*Base*.—Attenuate.

*Margin*.—Entire.

*Texture and luster, upper and lower surfaces*.—Sparsely pubescent; semi-glossy.

*Venation pattern*.—Pinnate.

*Color*.—Developing leaves, upper and lower surfaces: Close to NN137A. Fully developed leaves, upper surface: Close to NN137A; venation, close to 144A. Fully developed leaves, lower surface: Close to NN137C; venation, close to 144A.

Flower description:

*Flower arrangement and habit*.—Single flowers arranged on terminal and axillary racemes; freely flowering habit with about nine flowers per inflorescence and about 1,092 flowers developing per plant during the flowering season; flowers face mostly outwardly.

*Fragrance*.—None detected.

*Natural flowering season*.—Plants flower continuously from July to September in The Netherlands; plants begin flowering about eleven weeks after planting; flowers not persistent.

*Inflorescence height*.—About 17 cm.

*Inflorescence diameter*.—About 5 cm.

*Flower diameter*.—About 2.5 cm by 2.8 cm.

*Flower depth (height)*.—About 1.3 cm.

*Flower buds*.—Length: About 1 cm. Diameter: About 2 mm. Shape: Elongated oblong. Texture and luster: Smooth, glabrous; matte. Color: Close to NN155D.

*Petals*.—Arrangement: Four in a single whorl. Length: About 1.4 cm. Width: About 6 mm. Shape: Oblanceolate. Apex: Acute. Base: Attenuate. Margin: Entire. Texture and luster, upper and lower surfaces: Smooth, glabrous; matte. Color: When opening, upper and lower surfaces: Close to NN155D. Fully opened, upper surface: Close to NN155D; apices, close to 65C; venation, close to NN155D; color becoming closer to 65A with subsequent development. Fully opened, lower surface: Close to NN155D; apices, close to 65B; venation, close to NN155D; color becoming closer to 64A with subsequent development.

*Sepals*.—Arrangement: Four in a single whorl. Length: About 1.3 cm. Width: About 2 mm. Shape: Linear. Apex: Acute. Base: Truncate. Margin: Entire. Texture and luster, upper surface: Pubescent; semi-glossy. Texture and luster, lower surface: Smooth, glabrous; semi- glossy. Color, upper and lower surfaces: Close to 144C with apices, close to 181A.

*Pedicels*.—Length: About 1 cm. Diameter: About 1 mm. Strength: Flexible. Aspect: About 40° from stem axis. Texture and luster: Pubescent; glossy. Color: Close to 143B.

*Reproductive organs*.—Stamens: Quantity: Eight per flower. Filament length: About 8 mm. Filament color: Close to NN155D. Anther shape: Linear; basifixed. Anther size: About 0.5 mm by 3 mm. Anther color: Close to 187A. Pollen amount: Abundant. Pollen color: Close to 4B. Pistils: Quantity: One per flower. Pistil length: About 1.2 cm. Style length: About 1.1 cm. Style color: Close to NN155D. Stigma shape: Four-lobed. Stigma diameter: About 1 mm. Stigma color: Close to 154B. Ovary color: Close to 53A. Fruits: Length: About 8 mm. Diameter: About 3 mm. Texture: Smooth, glabrous. Color: Close to 141A.

Garden performance: Plants of the new *Gaura* have been observed to have good garden performance and tolerate wind, rain and temperatures ranging from about −23° C. to about 35° C. and to be suitable for U.S.D.A. Hardiness Zones 6 to 10.

Pathogen & pest resistance: To date, plants of the new *Gaura* have not been observed to be resistant to pathogens and pests common to *Gaura* plants.

It is claimed:

1. A new and distinct *Gaura* plant named 'Dogaurgrabl' as illustrated and described.

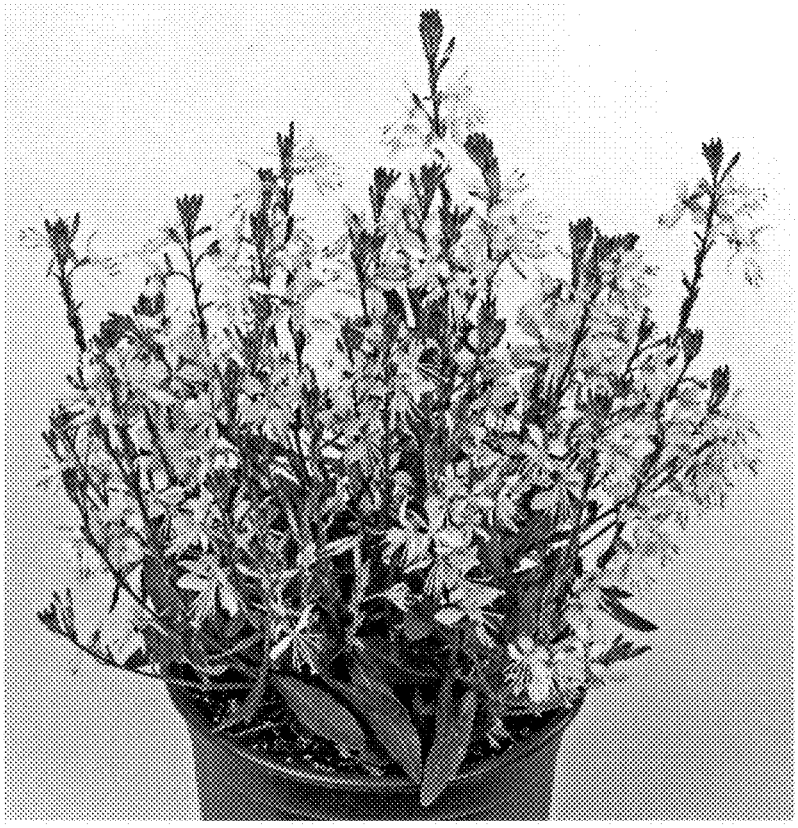

* * * * *